United States Patent [19]
Jones

[11] Patent Number: 5,925,320
[45] Date of Patent: *Jul. 20, 1999

[54] AIR PURIFICATION SYSTEM

[76] Inventor: John P. Jones, 500 Transmountain Rd. D17, Canutillo, Tex. 79835

[*] Notice: This patent issued on a continued prosecution application filed under 37 CFR 1.53(d), and is subject to the twenty year patent term provisions of 35 U.S.C. 154(a)(2).

[21] Appl. No.: 08/868,714

[22] Filed: Jun. 4, 1997

[51] Int. Cl.⁶ ..................................................... A61L 2/10
[52] U.S. Cl. ........................ 422/121; 422/24; 422/186.3; 55/327; 55/331; 96/16; 250/504 R
[58] Field of Search ........................... 422/24, 121, 186.3; 55/279, 327, 331; 96/16; 250/504 R; 454/906; 181/224, 225

[56] References Cited

U.S. PATENT DOCUMENTS

| | | | |
|---|---|---|---|
| 2,150,263 | 3/1939 | Chesney | 250/46 |
| 2,820,406 | 1/1958 | Argentieri | 454/906 |
| 2,886,121 | 5/1959 | Welbourn | 181/225 |
| 3,125,286 | 3/1964 | Sanders | 181/224 |
| 4,102,654 | 7/1978 | Pellin | 55/102 |
| 4,403,370 | 9/1983 | Rapp | 181/224 |
| 5,606,495 | 2/1997 | Jaidka | 364/184 |

OTHER PUBLICATIONS

"UVC–Control, Air Borne Micro–Organisms", Sun Twin, No Date Listed or Available.
"CST–1000 Operation Manual—Clear–Aire Air Purifier", Indoor Quality, Inc. No Date Listed or Available.

*Primary Examiner*—Krisanne Thornton
*Assistant Examiner*—Fariborz Moazzam
*Attorney, Agent, or Firm*—Grace J. Fishel

[57] ABSTRACT

An air purification system comprises a housing, a generally S-shaped duct mounted within the housing, at least one blower mounted within the housing for circulating air through the system, and purification structure for removing contaminants from the air. The system preferably comprises two blowers, a master control switch for activating one of the blowers to circulate air through the filter, and a secondary control switch for activating the other blower and the UVC source to initiate a UVC purification process to further purify the filtered air.

12 Claims, 2 Drawing Sheets

AIR PURIFICATION SYSTEM

BACKGROUND OF THE INVENTION

This invention relates to a system for enhancing ambient air quality, and more specifically is directed to a method and apparatus for sterilizing and purifying the ambient air.

Air contamination and pollution is a long-standing problem which afflicts everyone to varying degrees. In urban areas, pollution levels continue to rise. Even in rural areas, contaminants, such as mold, pollen, and bacteria, exist in the air. Air contamination presents serious long-term health risks. Contaminants also afflict persons suffering from allergies, asthma, emphysema, and many more respiratory related illnesses.

Filters have been used to remove particulate contaminants, such as smoke, dust, pollen, and lint. Filters are designed to filter out contaminants of a specific size or larger.

It is also known that ozone breaks down other contaminants, such as viruses, bacteria, mold spores. Ozone having a high energy level ("photozone") breaks up gasses and odors, and destroys pathogens.

Others have attempted with varying degrees of success to devise methods and devices for improving air quality by creating ozone. Such prior art methods and devices suffer significant disadvantages.

It is known that applying a substantial voltage between two points creates sparking, similar to lightning. The sparking reacts with ambient air to create ozone. However, this method creates a serious health risk. The heated sparks cause heated nitrogen gas to form. The heated nitrogen gas reacts with the ambient air to form nitric oxide. When nitric oxide is ingested by humans (or animals for that matter), moisture from the lung causes the nitric oxide to turn into nitric acid. Nitric acid can cause many adverse reactions.

Another known method for creating ozone employs polarized plates, one positively charged and the other negatively charged. The electric field between the polarized plates creates ozone. However, contaminates deposit on the plates over time and cause sparks which causes nitrous gasses to form with the same adverse effects described above.

It is also known that ozone can be created without forming nitrous gasses by eliminating the use of heat (known as "cold process"). By this method, ozone can be created by subjecting air (or water) to high frequency electromagnetic energy or ultraviolet (UV) light. The amount and type of ozone created depends on the wavelength and intensity of the energy source. A light source (such as a UV lamp) omits a stream of invisible packets or compressions of energy, referred to as photons or waves. The energy carried by photons increases as the wavelength shortens.

Systems have been employed to create ozone by cold process, thereby avoiding nitrous gas omission. Such systems are intended for use in homes, hospitals, and other areas where it is desirable to remove contaminants. To create ozone (or photozone) by cold process, blowers must be employed to draw air into the system and direct the air past a light source (e.g., a UV lamp). The prior art systems are disadvantageous because they are noisy and consume more energy than necessary.

Prior art purification systems also suffer disadvantage by drawing air into the system, and directing the filtered air through and out of the system along a generally linear path. Such systems cause air turbulence and minimize uniformity of air exposure to the UV light source, which decreases the efficiency of the unit and creates additional noise.

SUMMARY OF THE INVENTION

An air purification system is disclosed which comprises a housing having a generally S-shaped air duct mounted within the housing. The system includes at least one blower secured to the housing for circulating air through the air duct and structure for removing contaminants from air. The system further comprises activation circuitry for activating and deactivating the blower and the system.

In the preferred embodiment, the structure for removing contaminants comprises two separate stages: a filter for removing contaminants mounted within the housing adjacent the inlet of the air duct; and a UV source secured in the bypass section of the air duct. The duct narrows from its inlet to a bypass section and widens from there to the duct outlet. The bypass section has a reflective surface to increase the efficiency of the unit.

The system may also include a secondary blower, coupled to the UV source for turning on the UV source when the secondary blower is activated and turning off the UV source when the secondary blower is deactivated. The secondary blower circulates air through the air purification filter and the duct inlet, past the UV source, and out the duct outlet, when the secondary blower is activated. Secondary activation circuitry activates and deactivates the secondary blower and UV source, and preferably comprises a timer switch which activates at preselected times, or a sensor switch which activates only when a contamination level exceeds a threshold value. A baffle can also be mounted on the housing between the master blower and the secondary blower to eliminate backdraft. This system and method of operation reduces the energy required to effectively purify the air, and reduces the noise level of the device at times when only one blower is operating.

As can be seen from the above, the system and method of the present invention maximize air purification, while minimizing noise and energy use. Other features will be in part apparent and in part pointed out hereinafter.

BRIEF DESCRIPTION OF THE DRAWINGS

In the accompanying drawings which form a part of the specification and are to be read in conjunction therewith and in which like reference numerals are used to indicate like parts in the various views.

DETAILED DESCRIPTION OF THE PREFERRED EMBODIMENTS

Figure 1:
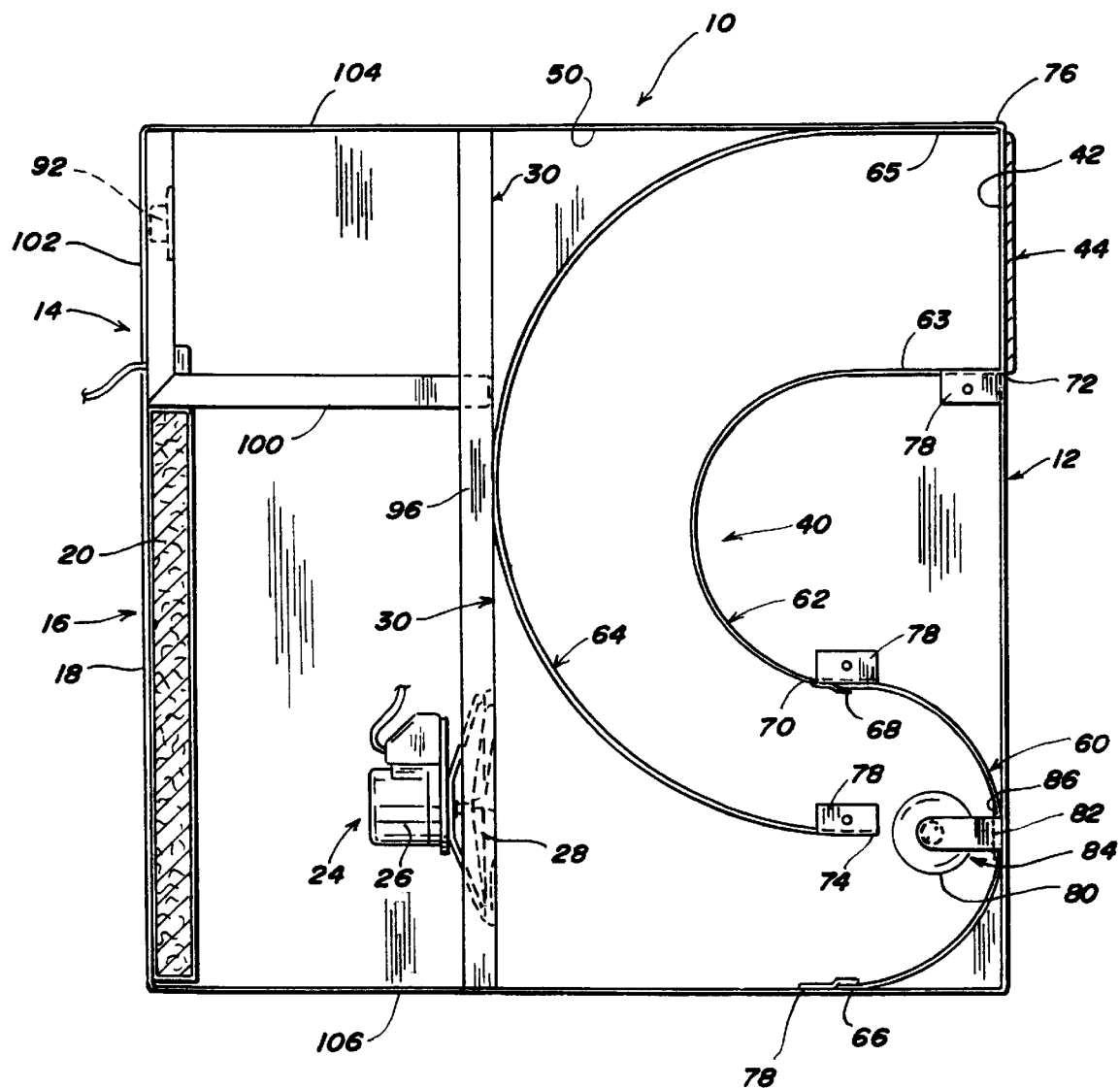
FIG. 1 is a cross-sectional side view of the improved purification system in accordance with the present invention.

FIG. 1 shows a side view of the improved purification system of the present invention. The system is enclosed in a housing generally designated 10. The housing is cube-shaped, having outside dimensions of roughly 14"×14"×14". The housing has a front face 12 and a back face 14.

The back face 14 has an intake opening 16 covered by an intake grate 18. Mounted behind grate 18 is a filter 20 for removing particulate contaminants contained in air passing through the filter.

Figure 2:
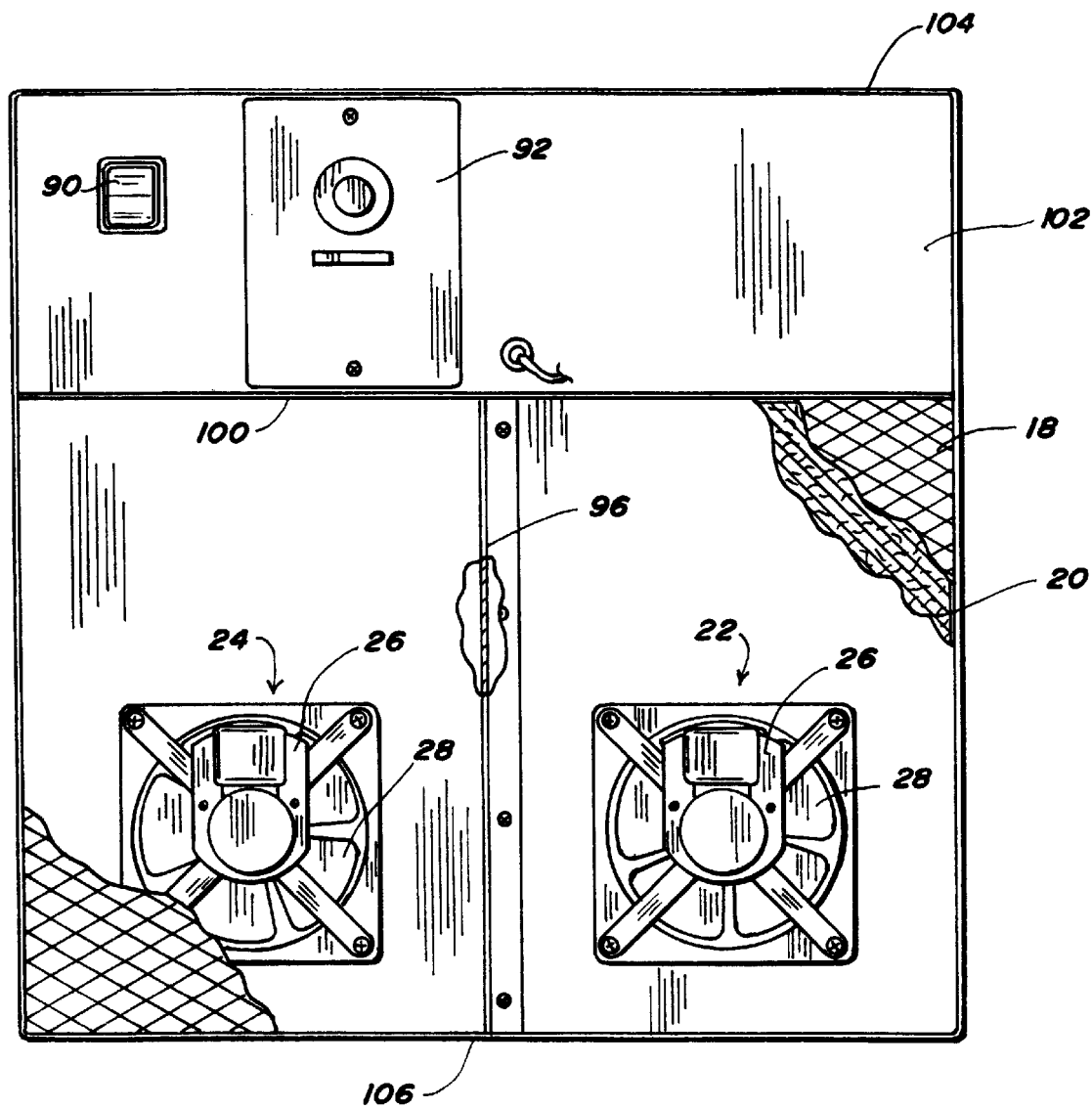
FIG. 2 is a rear elevation view of the purification system, with break-away portions to show internal areas of the system.

In the preferred embodiment, air is drawn through the intake opening 16 and through filter 20 by two blowers (shown in FIG. 2—a master blower 24 and a secondary blower 22). As described below, the use of two blowers provides more efficient operation of the improved purification system of the present invention. Each blowers has a motor 26 for driving a fan blade 28 and is well known in the art. The blowers 22 and 24 are mounted to partition member 30 of the housing by conventional means. Partition member 30 extends parallel to front face 12 of housing 10.

Blowers 22 and 24 draw air through filter 20 and direct the air through an air duct designated generally 40. The air is directed past a UV source 80, preferably an ultraviolet C-band (UVC) source, to create ozone or photozone molecules (not shown), which are directed through duct 40 and through an outlet opening 42. Outlet opening 42 is covered by an outlet grate 44 to prevent debris from entering the air duct. Air duct 40 is formed within housing 10 in a compartment 50 in front of the partition member 30. Outlet opening 42 and outlet grate 44 extend across the upper portion of front face 12 as shown in FIG. 1.

The air duct 40 is preferably formed by three preformed sheet metal sections designated 60, 62, and 64. Section 60 begins at point 66 and extends to point 68. Section 62 begins at point 70 and extends to point 72. Section 64 begins at point 74 and extends to point 76. The sections 60, 62, and 64 are secured together and within compartment 50 by conventional means such as brackets 78, screw fasteners or welding. As shown, the passageway formed by air duct 40 extends generally upward and transverse to front face 12.

The air duct 40 is generally S-shaped, directing the air through 360 degrees of turn, to minimize turbulence, thereby increasing efficiency and reducing noise.

The UVC source 80 extends parallel to the curved face of section 60. The UVC source is secured to section 60 by conventional means such as brackets 82. The brackets 82 space the outside surface 84 of UVC source 80 about 1.5 inches from the inner surface 86 of section 60. The distance between the outside surface 84 of UVC source 80 and the inside surface 86 of section 60 is preferably between about 1.5 inches and about 2.0 inches. This range optimally balances the amount of air flow between the UVC source and inner surface 86 of section 60, and the strength of the electromagnetic energy from the source reaching the inner surface 86. As the distance is increased, the strength of the UVC source reaching the inner surface 86, and its ability to purify passing ambient air at that position, decreases. At distances greater than 2 inches, more air is allowed to pass by the UVC source, but such air is not purified as effectively. As shown in FIG. 1, there is also a relief space between point 74 and the UVC lamp. This space should be about 1/8 of an inch long to facilitate replacing the UV lamp bulbs.

It is further noted that by mounting the UVC source in section 60, the ambient air is exposed to electromagnetic energy emitted by the UVC source 80 through more than 180 degrees of turn. This greatly increases the efficiency of the unit compared to directing air linearly past the UVC source and directly out of the front face 12 of the housing 10.

In the preferred embodiment, the inner surface 86 of section 60 is made of or coated with a reflective material. A reflective material minimizes absorption of the electromagnetic energy, thereby increasing the efficiency of the system to purify the ambient air. A highly polished stainless steel surface is preferred.

Section 60 generally forms a half cylinder which extends transverse to the front face 12 of housing 10. The radius of the half cylinder is preferably about 2 and ½ inches (2.5") for a housing having a 14" height. Section 62 comprises two sections: a half cylinder portion, preferably having a 2 and ½ inch (2.5") radius, and an extension portion 63, extending to the front face 12 of housing 10. Section 62 also extends transversely to front face 12 between the side panels of housing 10. Section 64 is configured identically to section 62, except larger. Section 64 forms a half cylinder portion having about a 5 and ¾ inch (5.75") radius, and an extension portion 65 extending to the front face 12 of housing 12. The dimensions of section 60, 62, and 64 can be adjusted accordingly for larger or smaller units, and are provided herein merely for maintaining exemplary ratios.

As can be seen from the foregoing, air is drawn into the generally S-shaped duct 40 at the inlet adjacent the blowers 22 and 24. The S-shaped duct narrows to the section where the air passes the UVC source, and then widens to outlet opening 42. Further, because the UVC source 80 is mounted in section 60 of the air duct 40, air is directed past the UVC source in an arcuate (as opposed to linear) path, thereby increasing the distance through which air is exposed to the UVC energy, and thus increasing system efficiency.

Referring to FIG. 2, the purification system includes a master activation switch 90. Master switch 90 is electrically connected to master blower 24. Switch 90 is operable to provide power to all electronic circuits, including activation of the master blower 24. When switch 90 is activated, blower 24 draws air through filter 20 and directs it through air duct 40 and out of the outlet opening 42.

Filter 20 removes particulate contaminants in the ambient air drawn through the filter. Suitable filters are well known in the art. For instance, a permanently magnetized, electrostatic filter can be used to remove particulate contaminants as small as 0.1 micron and larger. Such filters remove approximately 75% of particulate contaminants contained in ambient air, including smoke, dust, pollen, and lint. For greater filtration, an electronic media 700 volt filter can be used. An electronic media filter removes approximately 95% of all particulate contaminants as small as 0.01 micron or larger. An electronic media filter eliminates bacteria by removing portions of the particulate contaminants making up such elements. By efficiently removing particulate contaminants prior to directing the air past the UVC energy field, the system's sterilizing efficiency is improved.

In the preferred embodiment, a secondary activation switch 92 automatically controls operation of the secondary blower 22, and simultaneously activates and deactivates the UVC source 80. The secondary activation switch 92 is adapted to be programmed to automatically activate the secondary blower 22 and UVC source 80 at a predetermined time. Alternatively, switch 92 may include circuitry for sensing the level of ambient air contamination and automatically activating when a predetermined level of contamination is sensed.

The combination of master switch 90 and secondary switch 92 provides for 3-stage operation of the improved purification system. When master switch 90 is not activated, the purification system is deactivated entirely. When master switch 90 is activated, master blower 24 is activated to draw air through filter 20 and through the outlet opening 42, thereby purifying air drawn through the system; however, with switch 90 in the on position, secondary blower 22 and UVC source 80 are not activated. Only when master switch 90 and secondary switch 92 are on simultaneously are the secondary blower 22 and UVC source 80 activated. With both switches on, the improved purification system initiates a second purification function by directing the air filtered through filter 20 through the electromagnetic energy of UVC source 80, thereby further purifying the filtered air.

Preferably, secondary switch 92 automatically activates the second stage of purification only at designated times or when predetermined levels of contaminants are detected by switch 92. This procedure and arrangement conserves energy, reduces air flow, and reduces noise by operating the UVC purification stage only when necessary. Switch 92 assists in conserving energy and reducing noise when only one blower is activated. The UVC purification stage may however be performed whenever the purification system is activated by master switch 90. Further, switch 92 could be a manual "on/off" switch, thereby allowing the user to manually activate and deactivate the UVC purification stage. A combination of a manual and automatic switch could also be employed.

Switch 90 can be a single pole rocker switch. Switch 92 can be a 3-position slider switch, having on, off, and auto positions. Other suitable switches are well-known in the art.

The housing 10 also has a partition member 100 which extends transversely between back wall 102 and partition member 30, as shown in FIG. 1. The partition member 100, back wall 102, top wall 104, and partition member 30 form a compartment for the electrical switches and related circuitry.

The filtration system also preferably includes a baffle 96 (shown in FIG. 2) which extends vertically from the bottom wall 106 to the top wall 104, and perpendicularly rearward from partition member 30, preferably by at least approximately 4 inches. The partition member prevents backdraft through the common air intake opening 16. The baffle therefore increases efficiency of the system when operating in the mode in which only the master blower 24 is activated. The baffle also reduces noise caused by backdraft air turbulence.

The housing, air duct, and partition members can be made of stainless steel to prevent deterioration caused by oxidation. It has been determined that contaminants in the air deposit on the various surfaces of the purification system. The deposits facilitate oxidation formation, and stainless steel resists deterioration precipitated by oxidation.

From the foregoing, it will be seen that this invention is one well adapted to attain all the ends and objects hereinabove set forth together with other advantages which are obvious and which are inherent to the system.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interperted as illustrative and not in a limiting sense.

What is claimed is:

1. An air purification system comprising:
    a housing having an intake opening for permitting air to enter the housing and an outlet opening for permitting air to exit the housing;
    a curved hollow duct positioned at least partially inside the housing and having a passage extending between an inlet end in communication with the intake opening of the housing and an outlet end in communication with the outlet opening of the housing, the passage having a gradually decreasing cross sectional area between the inlet end and a narrow-most section positioned along the passage and a gradually increasing cross sectional area between the narrow section and the outlet end, the narrow-most section having opposite first and second sides, the passage curving at the narrow-most section so that said first side of the narrow-most section is concave;
    a blower in communication with the passage for drawing air through the housing intake opening and blowing air through the passage from the inlet end to the outlet end; and
    an ultraviolet energy source mounted in the narrow-most section parallel to said first side of the narrow-most section of the passage adjacent said second side so that substantially all of the air blown through the passage passes between the energy source and said first side of the narrow-most section in an arcuate path around said energy source.

2. An air purification system as set forth in claim 1 wherein said first side of the narrow-most section has an inner reflective surface.

3. An air purification system as set forth in claim 1 wherein the energy source and said first side of the narrow-most section are spaced by a distance of between about 1.5 and about 2.0 inches.

4. An air purification system as set forth in claim 1 wherein the energy source and said second side of the narrow-most section are spaced by a distance of about 0.125 inches.

5. An air purification system as set forth in claim 1 wherein the ultraviolet source is a UVC source.

6. An air purification system as set forth in claim 1 further comprising a filter mounted in the housing so that air blown through the passage passes through the filter.

7. An air purification system as set forth in claim 6 wherein the filter is mounted in the housing upstream from the ultraviolet energy source.

8. An air purification system as set forth in claim 7 wherein the filter is mounted at the intake opening of the housing.

9. An air purification system as set forth in claim 1 wherein the passage has a gradually increasing cross sectional area over more than half of a distance extending from the narrow-most section to the outlet end of the passage.

10. An air purification system as set forth in claim 1 wherein the curved narrow-most section turns the air through an arc of approximately 180 degrees.

11. An air purification system as set forth in claim 1 wherein the passage is curved between the narrow-most section and the outlet of the passage.

12. An air purification system as set forth in claim 11 wherein the passage between the narrow-most section and the outlet turns the air through an arc of approximately 180 degrees.

\* \* \* \* \*